United States Patent
Chiang et al.

(10) Patent No.: US 11,690,883 B2
(45) Date of Patent: Jul. 4, 2023

(54) ***LACTOBACILLUS ACIDOPHILUS* TW01 ISOLATE AND USE THEREOF**

(71) Applicant: I EATING LIGHT LTD., Kaohsiung (TW)

(72) Inventors: Hsin-Hua Chiang, Kaohsiung (TW); Bo-Jyun Liou, Kaohsiung (TW)

(73) Assignee: I EATING LIGHT LTD., Kaohsiung (TW)

( * ) Notice: Subject to any disclaimer, the term of this patent is extended or adjusted under 35 U.S.C. 154(b) by 0 days.

(21) Appl. No.: 17/736,387

(22) Filed: May 4, 2022

(65) Prior Publication Data

US 2022/0370524 A1 Nov. 24, 2022

(30) Foreign Application Priority Data

May 10, 2021 (TW) .................. 110116826

(51) Int. Cl.
*A61K 35/747* (2015.01)
*A23L 33/135* (2016.01)
*C12R 1/23* (2006.01)
*A23L 33/00* (2016.01)

(52) U.S. Cl.
CPC .......... *A61K 35/747* (2013.01); *A23L 33/135* (2016.08); *A23L 33/40* (2016.08); *A23V 2002/00* (2013.01); *A23V 2200/32* (2013.01); *A23V 2200/324* (2013.01); *A23Y 2220/03* (2013.01); *C12R 2001/23* (2021.05)

(58) Field of Classification Search
CPC ..... A61K 35/747; A23L 33/135; A23L 33/40; A23V 2002/00; A23V 2200/32; A23V 2200/324; A23Y 2220/03; C12R 2001/23
See application file for complete search history.

(56) References Cited

U.S. PATENT DOCUMENTS

2018/0296582 A1\* 10/2018 von Maltzahn ...... A61K 31/047

\* cited by examiner

*Primary Examiner* — Louise W Humphrey
*Assistant Examiner* — Alexander M Duryee
(74) *Attorney, Agent, or Firm* — Nixon & Vanderhye

(57) ABSTRACT

Disclosed herein is an isolated strain of *Lactobacillus acidophilus* TW01, which is deposited at Deutsche Sammlung von Mikroorganismen and Zellkulturen GmbH under an accession number DSM 33990. Also disclosed herein are uses of the isolated strain of *Lactobacillus acidophilus* TW01 for alleviating an inflammation-related disorder and for improving gut health.

7 Claims, 2 Drawing Sheets

Specification includes a Sequence Listing.

LACTOBACILLUS ACIDOPHILUS TW01 ISOLATE AND USE THEREOF

CROSS-REFERENCE TO RELATED APPLICATION

This application claims priority of Taiwanese Invention Patent Application No. 110116826, filed on May 10, 2021.

FIELD

The present disclosure relates to an isolated strain of *Lactobacillus acidophilus* TW01, which has been deposited at Deutsche Sammlung von Mikroorganismen und Zellkulturen GmbH under an accession number DSM 33990. The present disclosure also relates to use of the isolated strain of *Lactobacillus acidophilus* TW01 for alleviating an inflammation-related disorder and for improving gut health.

BACKGROUND

Probiotics are resident normal flora of the intestinal tract and believed to play important roles in regulating proper intestinal immunity and digestion by balancing intestinal microflora. These beneficial microorganisms are widely used as live microbial dietary supplements and can help restore intestinal microfloral balance. Many species of lactic acid bacteria (LAB) are conferred with the generally recognized as safe (GRAS) status, and are widely used as probiotics.

Common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc. LAB have been shown to be capable of inhibiting the growth of pathogenic bacteria in the gastrointestinal tract and alleviating lactose intolerance, and to have anti-cancer, anti-bacterial, anti-fatigue, and blood pressure lowering effects.

*Lactobacillus acidophilus* is one of the most commonly recognized species of the genus *Lactobacillus* in LAB and exists in the gastrointestinal tract and vagina of humans and animals. The health benefits associated with *Lactobacillus acidophilus* include reduction of gastrointestinal symptoms in lactose-intolerant individuals, relief from symptoms of constipation, competitiveness against pathogenic bacteria, reduction of cholesterol biosynthesis, treatment of infantile diarrhea, and antimicrobial activity against *Helicobacter pylori*, *Candida albicans*, and different species of molds.

SUMMARY

In a first aspect, the present disclosure provides a method for alleviating an inflammation-related disorder, which can alleviate at least one of the drawbacks of the prior art, and which includes administering to a subject in need thereof a composition including an isolated strain of *Lactobacillus acidophilus* TW01. The isolated strain of *Lactobacillus acidophilus* TW01 is deposited at Deutsche Sammlung von Mikroorganismen und Zellkulturen GmbH under an accession number DSM 33990.

In a second aspect, the present disclosure provides a method for improving gut health, which can alleviate at least one of the drawbacks of the prior art, and which includes administering to a subject in need thereof a composition including the abovementioned isolated strain of *Lactobacillus acidophilus* TW01.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
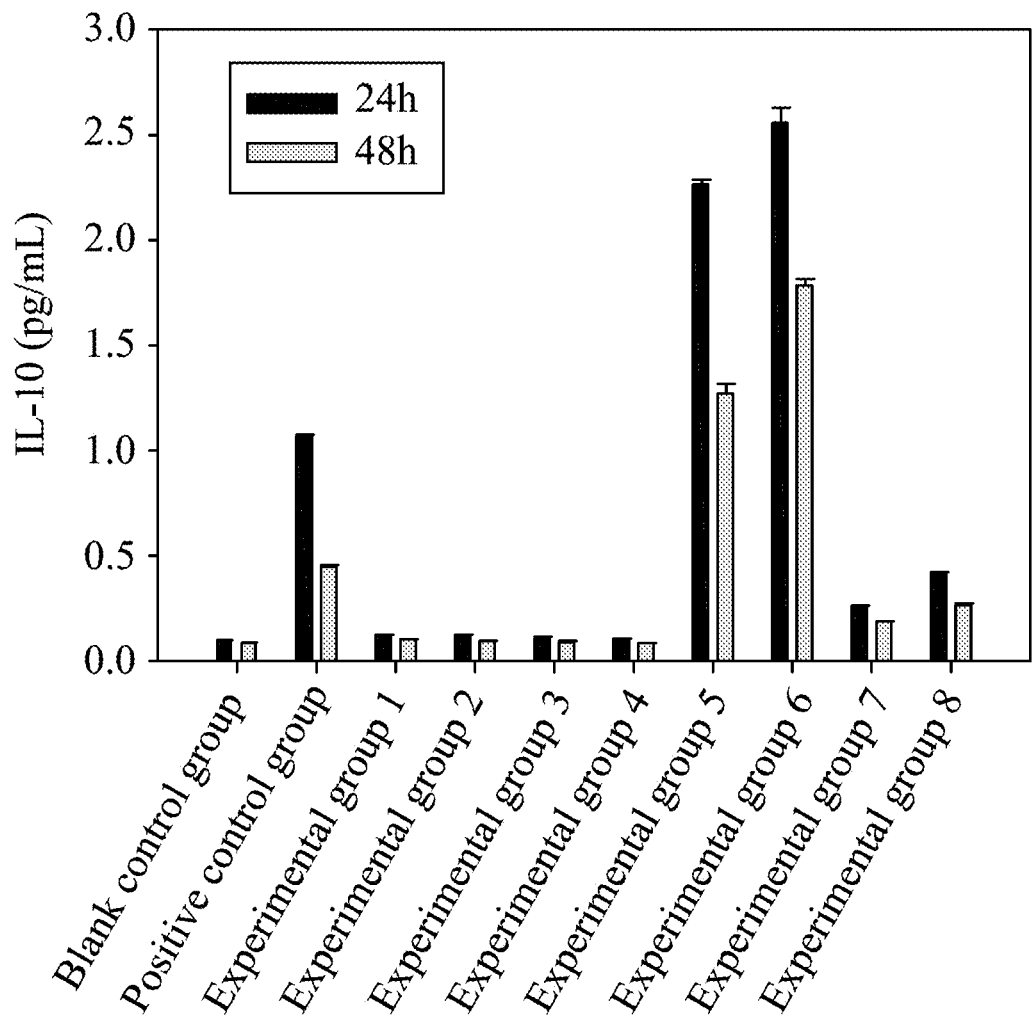
FIG. 1 shows the interleukin-10 (IL-10) content in each group of Example 3, infra.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

The present disclosure provides an isolated strain of *Lactobacillus acidophilus* TW01, which has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 911039 since Mar. 5, 2021, and which has also been deposited at the Deutsche Sammlung von Mikroorganismen und Zellkulturen (DSMZ) GmbH (Inhoffenstr. 7B, D-38124 Braunschweig, Germany) under an accession number DSM 33990 since Aug. 2, 2021 in accordance with the Budapest Treaty.

According to the present disclosure, the isolated strain of *Lactobacillus acidophilus* TW01 may be live cells or dead cells, concentrated or non-concentrated, a liquid, a paste, a semi-solid, a solid (e.g., a pellet, a granule, or a powder), and may be heat-inactivated, frozen, dried, or freeze-dried (e.g., may be in freeze-dried form or spray/fluid bed dried form). In an exemplary embodiment, the isolated strain of *Lactobacillus acidophilus* TW01 is in a liquid form. In another exemplary embodiment, the isolated strain of *Lactobacillus acidophilus* TW01 is present in the form of live cells.

The present disclosure also provides a method for alleviating an inflammation-related disorder, which includes administering to a subject in need thereof a composition including the aforesaid isolated strain of *Lactobacillus acidophilus* TW01.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "administering" or "administration" means introducing, providing or delivering the abovementioned composition to a subject showing condition(s) or symptom(s) of an inflammation-related disorder by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

As used herein, the terms "inflammation-related disorder" and "immune-related disorder" can be used interchangeably.

According to the present disclosure, the inflammation-related disorder may be selected from the group consisting of allergy (e.g., allergic rhinitis), asthma, arthritis, psoriasis, atopic dermatitis, systemic lupus erythematosus, inflammatory bowel disease (IBD) (e.g., colitis and Crohn's disease), and combinations thereof.

According to the present disclosure, the composition may be formulated as a food product using a standard technique well known to one of ordinary skill in the art. For example, the composition may be directly added to an edible material or may be used to prepare an intermediate composition (e.g., a food additive or a premix) suitable to be subsequently added to the edible material.

As used herein, the term "food product" refers to any article or substance that can be ingested by a subject into the body thereof. Examples of the food product may include, but are not limited to, fluid milk products (e.g., milk and concentrated milk), fermented milk (e.g., yogurt, sour milk, and frozen yogurt), milk powder, butter, beverages (e.g., tea and coffee), functional beverages, flour products, baked foods, confectionery, candies, health foods, animal feeds, and dietary supplements.

According to the present disclosure, the composition may be prepared in the form of a pharmaceutical composition. The pharmaceutical composition may be formulated into a suitable dosage form for oral, parenteral or topical administration using technology well known to those skilled in the art.

According to the present disclosure, the suitable dosage form for oral administration includes, but is not limited to, sterile powders, tablets, troches, lozenges, sustained film-coated tablets, oral ointments, pellets, capsules, dispersible powders or granules, solutions, suspensions, emulsions, syrup, elixir, slurry, drops, and the like.

For parenteral administration, the pharmaceutical composition according to the present disclosure may be formulated into an injection, e.g., a sterile aqueous solution or a dispersion.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration. In certain embodiments, the pharmaceutical composition may be administered via intralesional injection.

According to the present disclosure, the pharmaceutical composition may be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

The present disclosure further provides a method for improving gut health, which includes administering to a subject in need thereof the aforesaid composition.

In certain embodiments, the composition for improving gut health is a pharmaceutical composition. The pharmaceutical composition may be formulated into a suitable dosage form for oral or parenteral administration. The oral dosage form, parenteral dosage form, and pharmaceutically acceptable carrier of this pharmaceutical composition are similar to those described above for the pharmaceutical composition for alleviating an inflammation-related disorder.

In other embodiments, the composition for improving gut health is a food product as described above.

The dose and frequency of administration of the composition according to the present disclosure may vary depending on the following factors: the severity of the illness or disorder to be treated, routes of administration, and age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:

1. Ox-bile (dehydrated, purified fresh bile), sodium chloride, and glycerol used in the following experiments were purchased from Sigma-Aldrich.

2. Agar, BD Difco™ Lactobacilli MRS (De Man, Rogosa and Sharpe) broth, and tryptic soy broth used in the following experiments were purchased from BD (Becton, Dickinson and Company) Biosciences.

3. API® 50 CHL microbial identification kit was purchased from Creative Life Science Co., Ltd., Taiwan.

4. The lactobacilli MRS agar medium used in the following experiments was prepared by adding 1.5% agar to BD Difco™ Lactobacilli MRS broth.

5. Murine macrophage cell line RAW 264.7 was purchased from the Bioresource Collection and Research Center (BCRC) of the Food Industry Research and Development Institute (FIRDI) (No. 331, Shih-Pin Rd., Hsinchu City 300, Taiwan). The RAW 264.7 cells (BCRC 60001) were grown in a 10-cm Petri dish containing Dulbecco's Modified Eagle's Medium (DMEM) (Cat. No. D0819, Sigma-Aldrich) supplemented with 10% fetal bovine serum (FBS). The RAW 264.7 cells were cultivated in an incubator with culture conditions set at 37° C. and 5% $CO_2$. Medium change was performed every two to three days. Cell passage was performed when the cultured cells reached 80%-90% of confluence.

General Procedures:
1. Statistical Analysis

The experimental data are expressed as mean±standard deviation (SD). All the data were analyzed using SAS software, so as to evaluate the differences between the groups.

Example 1. Preliminary Screening of Lactic Acid Bacteria (LAB) Isolates

A. Source and Isolation of Tested Strains

Coffee grounds purchased from Gukeng Township (Yunlin, Taiwan) were subjected to a fermentation reaction, and the resultant coffee fermented broth was then mixed with a suitable amount of a 0.85% saline solution, so as to obtain a dilution (prepared using a dilution factor of $10^5$). 0.1 mL of the dilution was evenly spread onto Lactobacilli MRS agar medium, followed by cultivation under an anaerobic condition in an incubator at 37° C. for 72 hours.

Six LAB isolates were randomly selected from the MRS agar medium, and were designated as F2-2, F3-4, S2-1, K1-2, B-1, and D-1, respectively. These isolates were subjected to the analyses below.

B. Preparation of Bacterial Suspension of LAB Isolate

A respective one of the six LAB isolates obtained in section A of this example was inoculated in BD Difco™ Lactobacilli MRS broth, and was then cultivated under an anaerobic condition in an incubator at 37° C. for 24 hours to obtain a culture. After centrifugation at 1,200 g for 10 minutes, the resultant cell pellet was collected, and was washed with a 0.85% sterile saline solution, followed by centrifugation at 1,200 g for 10 minutes. The aforesaid washing and centrifugation steps were repeated twice.

After removal of the supernatant, the bacterial cells were re-suspended in a suitable amount of a 0.85% sterile saline solution, so as to obtain a bacterial suspension having a bacterial concentration of $1 \times 10^8$ CFU/mL. The six bacterial suspensions thus obtained were used for the following experiment.

Example 2. Acid Tolerance Test and Bile Salt Tolerance Test on LAB Isolates

Experimental Procedures:
A. Acid Tolerance Test

A 0.85% sterile saline solution was adjusted to pH 2.0 through addition of a 5 N hydrochloric acid solution and a 0.1 N sterile sodium hydroxide solution, so as to obtain an acid resistance test solution. 1 mL of a respective one of the six bacterial suspensions prepared in section B of Example 1 was mixed with 1.5 mL of a 0.85% sterile saline solution and 5 mL of the acid resistance test solution, followed by cultivation in an incubator (37° C.) for a total period of 60 minutes. On the 30th and 60th minutes after cultivation, 100 µL of the resultant cell culture was collected, and the number of surviving bacterial cells was counted using a spread plate protocol well-known to those skilled in the art. The log value of the colony forming unit (CFU) was further calculated and the viable cell count was indicated by log CFU/mL.

B. Bile Salt Tolerance Test

A sterile saline solution containing 0.3% (w/v) Ox-bile (dehydrated, purified fresh bile) was adjusted to pH 8.0 through addition of a 0.1 N sterile sodium hydroxide solution, so as to obtain a simulated bile salt solution. 1 mL of a respective one of the six bacterial suspensions prepared in section B of Example 1 was mixed with 1.5 mL of a 0.85% sterile saline solution and 5 mL of the simulated bile salt solution, followed by cultivation in an incubator (37° C.) for 240 minutes. Thereafter, 100 µL of the resultant cell culture was collected, and the number of surviving bacterial cells was counted using a spread plate protocol well-known to those skilled in the art. The log value of the colony forming unit (CFU) was further calculated and the viable cell count was indicated by log CFU/mL.

Results:

As shown in Table 1 below, on the 30th minute after cultivation in an acidic environment (pH 2), the viable cell count of LAB isolate B-1 was higher than those of LAB isolates F3-4, S2-1, K1-2, and D-1. On the $60^{th}$ minute after cultivation in an acidic environment (pH 2), LAB isolates F3-4, K1-2, and B-1 still exhibited good survivability.

In addition, after cultivation in an environment containing 0.3% (w/v) Ox-bile for 240 minutes, LAB isolates F2-2, F3-4, S2-1, B-1, and D-1 exhibited excellent survivability. These results indicate that LAB isolates F3-4, S2-1, B-1, and D-1 are able to overcome the environmental pressure posed by the human gastrointestinal tract, and hence can reach and colonize the intestine(s) after ingestion.

According to these results, the Applicant selected LAB isolates F3-4, S2-1, B-1, and D-1 for further experimentation to evaluate the anti-inflammatory activities of these strains.

TABLE 1

| LAB isolate | Acid tolerance test | | Bile salt tolerance test |
|---|---|---|---|
| | Viable cell count (log CFU/mL) | | |
| | $30^{th}$ minute | $60^{th}$ minute | $240^{th}$ minute |
| F2-2 | Not determined | Not determined | 6.66 ± 0.11 |
| F3-4 | 4.11 ± 0.12 | 3.94 ± 0.03 | 7.17 ± 0.08 |
| S2-1 | 3.20 ± 0.10 | Not determined | 7.78 ± 0.10 |
| K1-2 | 3.52 ± 0.15 | 1.49 ± 1.07 | Not determined |
| B-1 | 7.68 ± 0.03 | 1.33 ± 0.94 | 6.06 ± 0.13 |
| D-1 | 2.78 ± 0.13 | Not determined | 6.56 ± 0.10 |

Example 3. Evaluation of the Ability of LAB Isolates to Stimulate Secretion of Interleukin-10 (IL-10) and Interleukin-12 (IL-12) by Macrophages Experimental Procedures:
A. Preparation of Test Sample of LAB Isolate Each of the bacterial suspensions of LAB isolates F3-4, S2-1, B-1, and D-1 prepared in section B of Example 1 was subjected to a freeze-drying treatment, so as to obtain a freeze-dried powder of LAB isolate F3-4, a freeze-dried powder of LAB isolate S2-1, a freeze-dried powder of LAB isolate B-1, and a freeze-dried powder of LAB isolate D-1. A respective one of the four freeze-dried powders was mixed with a suitable amount of BD Difco™ Lactobacilli MRS broth, and the resultant test sample was subjected to the following experiments.

B. Determination of Contents of IL-10 and IL-12

The RAW 264.7 cells prepared in section 5 of "General Experimental Materials" were divided into 10 groups, including one blank control group, one positive control group, and eight experimental groups (i.e., experimental groups 1 to 8). Each group of the RAW 264.7 cells was incubated in a respective well of a 24-well culture plate containing 5 mL of DMEM supplemented with 10% FBS at $6.25 \times 10^5$ cells/well, followed by cultivation in an incubator (37° C., 5% $CO_2$) for 48 hours. Afterwards, each of the cell cultures of the eight experimental groups and positive control group was treated with the corresponding treating agent so that the cell culture of each group had a final concentration of the corresponding treating agent shown in Table 2. The cell culture of the blank control group received no treatment.

Each group was cultivated in an incubator (37° C., 5% $CO_2$) for a total period of 48 hours. On the $24^{th}$ and $48^{th}$ hours after cultivation, 5 mL of the respective resultant cell culture was collected, and was then subjected to centrifugation at 3,000 rpm for 15 minutes. The resultant supernatant was collected, and was then subjected to determination of IL-10 and IL-12 contents using an IL-10 enzyme-linked immunosorbent assay (ELISA) kit (Cat. No. EHIL10, Invitrogen) and an IL-12 ELISA kit (Cat. No. KAC1568, Invitrogen) in accordance with the manufacturer's instructions.

TABLE 2

| Group | Treating agent | Final concentration (pg/mL) |
|---|---|---|
| Blank control group | — | 0 |
| Positive control group | Lipopolysaccharide (LPS) | 100 pg/mL |
| Experimental group 1 | Test sample of LAB isolate S2-1 | 100 pg/mL |
| Experimental group 2 | Test sample of LAB isolate S2-1 | 200 pg/mL |
| Experimental group 3 | Test sample of LAB isolate F3-4 | 100 pg/mL |
| Experimental group 4 | Test sample of LAB isolate F3-4 | 200 pg/mL |
| Experimental group 5 | Test sample of LAB isolate B-1 | 100 pg/mL |
| Experimental group 6 | Test sample of LAB isolate B-1 | 200 pg/mL |
| Experimental group 7 | Test sample of LAB isolate D-1 | 100 pg/mL |
| Experimental group 8 | Test sample of LAB isolate D-1 | 200 pg/mL |

Figure 2:
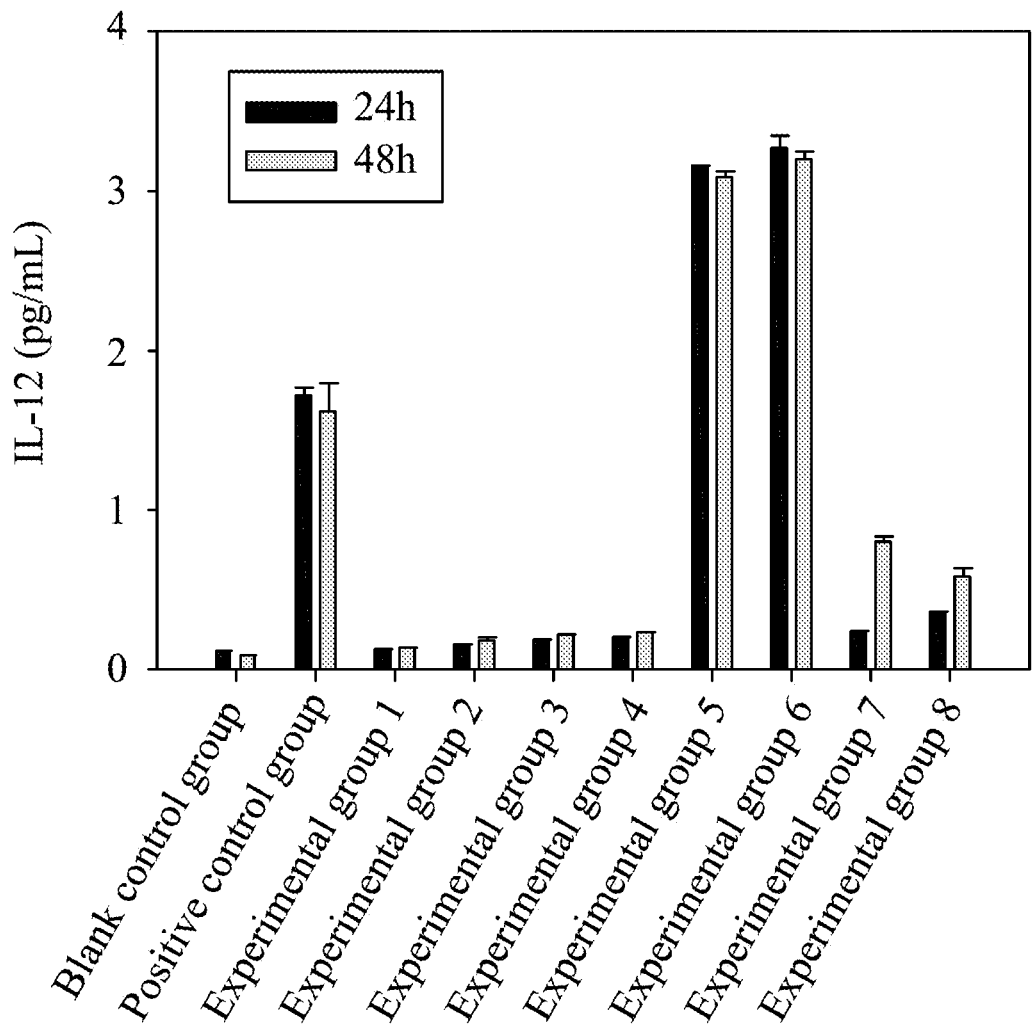
FIG. 2 shows the IL-12 content in each group of Example 3, infra.

Results:

Referring to FIGS. 1 and 2, the contents of IL-10 and IL-12 determined in the experimental groups 5 and 6 were higher than those determined in the experimental groups 1 to 4 and 7 to 8 and the positive control group, indicating that the ability of LAB isolate B-1 to stimulate secretion of IL-10 and IL-12 from macrophages is better than that of other LAB isolates. Therefore, LAB isolate B-1, having a greater potential for development, was subjected to characteristic analysis described below.

Example 4. Characteristic Analysis of LAB Isolate B-1

In order to identify the bacterial species of LAB isolate B-1, the following preliminary characteristic determination, 16S rDNA sequence analysis, and carbohydrate fermentation profiling were conducted.

A. Preliminary Tests

Items of the preliminary tests conducted for LAB isolate B-1 included: gram staining, morphological observation, mobility, catalase test, growth under aerobic and anaerobic conditions, and ability to produce an endospore.

The results of the aforesaid preliminary tests indicate that LAB isolate B-1 is gram-positive, non-motile, and catalase-negative, grows under anaerobic conditions, and is non-endospore forming. The cells of LAB isolate B-1 are coccus-shaped or rod-shaped.

B. 16S rDNA Sequence Analysis

Genomic DNA of LAB isolate B-1 was extracted using Genomic DNA Purification Kit (BioVision, Cat. No. K1457). The thus obtained genomic DNA was used as a template and was subjected to polymerase chain reaction (PCR) that was performed using a designed primer pair specific for 16S ribosomal DNA (rDNA) and the reaction conditions shown in Table 3, thereby obtaining a PCR product having a size of approximately 1460 bp.

TABLE 3

| Contents | | Volume (μL) |
|---|---|---|
| Genomic DNA of LAB isolate B-1 (10 ng) | | 1 |
| 16S rDNA-specific primer pair | Forward primer 27F (10 μM): 5'-agagtttgatcctggctcag-3' (SEQ ID NO: 1) | 0.5 |
| | Reverse primer 1492R (10 μM): 5'-ggttaccttgttacgact-3' (SEQ ID NO: 2) | 0.5 |
| dNTPs (10 mM) | | 0.5 |
| 10X buffer | | 2.5 |
| Taq DNA polymerase (5 U/μL) | | 0.5 |
| dd$H_2O$ | | 18.5 |

Operation conditions: denaturation at 94° C. for 5 min, followed by 30 cycles of the following reactions: denaturation at 95° C. for 60 sec, primer annealing at 50° C. for 60 sec, and extension at 72° C. for 60 sec; and lastly, elongation at 72° C. for 8 min.

The resultant PCR product was subjected to 2% agarose gel electrophoresis analysis for molecular weight verification.

Thereafter, the PCR product was verified by sequencing analysis which was entrusted to Seeing Bioscience Co., Ltd., Taiwan, so as to obtain the 16S rDNA sequence (SEQ ID No: 3) of LAB isolate B-1. Through comparison with the data in the NCBI's gene database, it was found that the 16S rDNA sequence of LAB isolate B-1 is most homologous to that of *Lactobacillus acidophilus*.

In view of the aforesaid experimental results, LAB isolate B-1 of the present disclosure is identified as *Lactobacillus acidophilus*.

C. Carbohydrate Fermentation Profiling

The carbohydrate fermentation profile of *Lactobacillus acidophilus* strain TW01 (i.e. LAB isolate B-1) was determined using API® 50 CHL identification system (bioMérieux). The result is shown in Table 4 below.

TABLE 4

| Carbohydrate | Capability of fermenting carbohydrate tested to produce acid |
|---|---|
| Glycerol | − |
| Erythritol | − |
| D-Arabinose | − |
| L-Arabinose | − |
| D-Ribose | − |
| D-Xylose | + |
| L-Xylose | + |
| D-Adonitol | − |
| Methyl-β-D-xylopyranoside | − |
| D-Galactose | − |
| D-Glucose | + |
| D-Fructose | + |
| D-Mannose | + |
| L-Sorbose | + |

TABLE 4-continued

| Carbohydrate | Capability of fermenting carbohydrate tested to produce acid |
|---|---|
| L-Rhamnose | + |
| Dulcitol | + |
| Inositol | − |
| D-Mannitol | − |
| D-Sorbitol | + |
| Methyl-α-D-mannopyranoside | + |
| Methyl-α-D-glucopyranoside | − |
| N-Acetylglucosamine | + |
| Amygdalin | + |
| Arbutin | + |
| Esculin | + |
| Salicin | + |
| D-Cellobiose | + |
| D-Maltose | + |
| D-Lactose | + |
| Melibiose | + |
| Sucrose | − |
| Trehalose | + |
| Inulin | + |
| Melezitose | − |
| Raffinose | + |
| Amidon | + |
| Glycogen | − |
| Xylitol | − |
| Gentiobiose | − |
| D-Turanose | + |
| D-Lyxose | + |
| D-Tagatose | − |
| D-Fucose | + |
| L-Fucose | − |
| D-Arabitol | − |
| L-Arabitol | − |
| Gluconate | − |

Note:
"+" indicates that *Lactobacillus acidophilus* strain TW01 is capable of fermenting the carbohydrate tested to produce an acid, whereas "−" indicates that the strain has no such capability.

Based on the aforementioned characterization results, the applicant believes that the *Lactobacillus acidophilus* strain TW01 is a strain of *Lactobacillus acidophilus*. As such, *Lactobacillus acidophilus* strain TW01 has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 911039 since Mar. 5, 2021, and has also been deposited at the Deutsche Sammlung von Mikroorganismen und Zellkulturen (DSMZ) GmbH (Inhoffenstraße 7B, 38124 Braunschweig, Germany) under an accession number DSM 33990 since Aug. 2, 2021 in accordance with the Budapest Treaty.

Summarizing the above test results, it is clear that *Lactobacillus acidophilus* TW01 of the present disclosure can increase the anti-inflammation-associated IL-10 and IL-12, and hence is capable of alleviating an inflammation-related disorder and modulating gut immunity.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

SEQUENCE LISTING

<110> I EATING LIGHT LTD.

<120> LACTOBACILLUS ACIDOPHILUS TW01 ISOLATE AND USE THEREOF amplification of

<130> PE-65633-AM

<160> 3

<170> PatentIn version 3.5

<210> 1

<211> 20

<212> DNA

<213> Artificial Sequence

<220>

<223> Forward primer 27F for PCR amplification of bacterial 16S rDNA fragment

<400> 1
agagtttgat cctggctcag    20

| SEQUENCE LISTING |
| --- |

<210> 2

<211> 18

<212> DNA

<213> Artificial Sequence

<220>

<223> Reverse primer 1492R for PCR amplification of
bacterial 16S rDNA fragment

<400> 2
ggttaccttg ttacgact                                         18

<210> 3

<211> 1468

<212> DNA

<213> *Lactobacillus acidophilus*

<400> 3

```
atgaagaaaa atagaaaatt tttaggttta gctgctgctg cattgttagc agttgcacct    60
gttgtaacta gtgccgtacc tgtaagtgct gacacaccaa cggtggaccc ggggttgtcg   120
aaacctgtaa attctccagc acaatcacaa gttactggtg ctactccatt cttctcatat   180
cagaatggta acccaattta ttctgccggt gaaocaccad acattaatgc tggttcattt   240
actactatcg gccaaattgt agatgcaatt aataagaaca ttgtctttgg tgaagctggc   300
tcaactggaa caactcgtca agaagatatt tcagctgcag aagtaattag acaattaaaa   360
gccgacagca agagtgttga aattaaaggc aacgatgcaa aggccacagt ttcaaaatta   420
ccagcaaaact ttgtaattac tttgaagcac actgtaaatg gtcaagctaa tactttgaat   480
gttcgtttct acactacttc tcaaccaaca gaatctgtag ataagtctgc tccagtattc   540
tacgtaactg aaggttcatc agctgctaag caagctactt caggtgcata ctaccaagta   600
gctgcaggct caaacttcaa cccattaagc ttcgtaaata gtaatggtga aactgtatca   660
ttctcagctc gtccagctga tggtaataac gctggtgcaa ctgtaagtgt tgcttctaac   720
ccagtagata ctaccaacgc aggtcgtttc tacactgtta cttttgactgc tactaacact   780
tcaaacaaga ctagccgcta ctcatacact gtattgattg tttcaaacgg tttacaaaaa   840
gtttatgata aatggtgcta gttcagcagc aacttacagc atttacggta accaagtttc   900
atcaaactca actaccttta aggatggtca agaagttcac gtaggtaaca ctacaagaac   960
tattaacaat gtatcatact caaaggtatc aactaagtct aaggcagatg ctgaccaagg  1020
taacctttgg attcaaactt cagctttgac tcaaactacc ccaaccactc cttcagacag  1080
caatgctgaa actcataatg taatggttga ctcacgtgct tacgacaagg acggtaacta  1140
cttaggccac atgtactacg catatgacaa cattgatatc gttccaactg ttgtaaccat  1200
caacggcaag acttactaca aggttgctaa caaggatgaa tatgtcagcg tcaccaacat  1260
caccggccac caacgtactt tacgtcacaa cgcttacatt tactggtcat cataccgtcg  1320
taccccaggt actggcaaga tgtacagagg ccaaactgta actacttacg gtcctgcaat  1380
```

-continued

```
gagattcaag aacggtaaga agtactacag aatccaaggc tgcagaaaca acaacaagcg    1440
ttacatcaag gctgcaaact tctattaa                                        1468
```

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Forward primer 27F for PCR amplification of
      bacterial 16S rDNA fragment

<400> SEQUENCE: 1

```
agagtttgat cctggctcag                                                   20
```

<210> SEQ ID NO 2
<211> LENGTH: 18
<212> TYPE: DNA
<213> ORGANISM: Artificial Sequence
<220> FEATURE:
<223> OTHER INFORMATION: Reverse primer 1492R for PCR amplification of
      bacterial 16S rDNA fragment

<400> SEQUENCE: 2

```
ggttaccttg ttacgact                                                     18
```

<210> SEQ ID NO 3
<211> LENGTH: 1468
<212> TYPE: DNA
<213> ORGANISM: Lactobacillus acidophilus

<400> SEQUENCE: 3

```
atgaagaaaa atagaaaatt tttaggttta gctgctgctg cattgttagc agttgcacct      60
gttgtaacta gtgccgtacc tgtaagtgct gacacaccaa cggtggaccc ggggttgtcg     120
aaacctgtaa attctccagc acaatcacaa gttactggtg ctactccatt cttctcatat     180
cagaatggta acccaatttta ttctgccggt gaaacaccaa acattaatgc tggttcattt     240
actactatcg gccaaattgt agatgcaatt aataagaaca ttgtctttgg tgaagctggc     300
tcaactggaa caactcgtca agaagatatt tcagctgcag aagtaattag acaattaaaa     360
gccgacagca agagtgttga aattaaaggc aacgatgcaa aggccacagt ttcaaaatta     420
ccagcaaact ttgtaattac tttgaagcac actgtaaatg gtcaagctaa tactttgaat     480
gttcgtttct acactacttc tcaaccaaca gaatctgtag ataagtctgc tccagtattc     540
tacgtaactg aaggttcatc agctgctaag caagctactt caggtgcata ctaccaagta     600
gctgcaggct caaacttcaa cccattaagc ttcgtaaata gtaatggtga aactgtatca     660
ttctcagctc gtccagctga tggtaataac gctggtgcaa ctgtaagtgt tgcttctaac     720
ccagtagata ctaccaacgc aggtcgtttc tacactgtta ctttgactgc tactaacact     780
tcaaacaaga ctagccgcta ctcatacact gtattgattg tttcaaacgg tttacaaaaa     840
gtttatgata aatggtgcta gttcagcagc aacttacagc atttacggta accaagtttc     900
atcaaactca actacctta aggatggtca agaagttcac gtaggtaaca ctacaagaac     960
```

-continued

```
tattaacaat gtatcatact caaaggtatc aactaagtct aaggcagatg ctgaccaagg    1020
taacctttgg attcaaactt cagctttgac tcaaactacc ccaaccactc cttcagacag    1080
caatgctgaa actcataatg taatggttga ctcacgtgct tacgacaagg acggtaacta    1140
cttaggccac atgtactacg catatgacaa cattgatatc gttccaactg ttgtaaccat    1200
caacggcaag acttactaca aggttgctaa caaggatgaa tatgtcagcg tcaccaacat    1260
caccggccac caacgtactt tacgtcacaa cgcttacatt tactggtcat cataccgtcg    1320
taccccaggt actggcaaga tgtacagagg ccaaactgta actacttacg gtcctgcaat    1380
gagattcaag aacggtaaga agtactacag aatccaaggc tgcagaaaca acaacaagcg    1440
ttacatcaag gctgcaaact tctattaa                                      1468
```

What is claimed is:

1. A method for alleviating an inflammation-related disorder, comprising administering to a subject in need thereof a composition including an isolated strain of *Lactobacillus acidophilus* TW01,
wherein the isolated strain of *Lactobacillus acidophilus* TW01 is deposited at Deutsche Sammlung von Mikroorganismen und Zellkulturen GmbH under an accession number DSM 33990.

2. The method as claimed in claim 1, wherein the composition is a food product or a pharmaceutical composition.

3. The method as claimed in claim 2, wherein the pharmaceutical composition is in a dosage form selected from the group consisting of an oral dosage form, a parenteral dosage form, and a topical dosage form.

4. The method as claimed in claim 1, wherein the inflammation-related disorder is selected from the group consisting of allergy, asthma, arthritis, psoriasis, atopic dermatitis, systemic lupus erythematosus, inflammatory bowel disease, and combinations thereof.

5. A method for improving gut health, comprising administering to a subject in need thereof a composition including an isolated strain of *Lactobacillus acidophilus* TW01,
wherein the isolated strain of *Lactobacillus acidophilus* TW01 is deposited at Deutsche Sammlung von Mikroorganismen und Zellkulturen GmbH under an accession number DSM 33990.

6. The method as claimed in claim 5, wherein the composition is a food product or a pharmaceutical composition.

7. The method as claimed in claim 6, wherein the pharmaceutical composition is in a dosage form selected from the group consisting of an oral dosage form and a parenteral dosage form.

* * * * *